United States Patent
Delnevo et al.

(10) Patent No.: US 7,727,391 B2
(45) Date of Patent: *Jun. 1, 2010

(54) EXTRACORPOREAL BLOOD TREATMENT MACHINE

(75) Inventors: Annalisa Delnevo, Sant'Agata Bolognese (IT); Francesco Ribolzi, Modena (IT); Claudio Tonelli, Modena (IT); Vincenzo Baraldi, Quistello (IT); Massimo Zaccarelli, San Felice Sul Panaro (IT); Jacques Chevallet, Serezin du Rhone (FR); Jacques Duchamp, Bron (FR); Aziz Aberkane, Decines (FR); Gabriel Meyssonnier, Dizimieu (FR); Dominique Pouchoulin, Tramoyes (FR)

(73) Assignee: Gambro Lundia AB (SE)

( * ) Notice: Subject to any disclaimer, the term of this patent is extended or adjusted under 35 U.S.C. 154(b) by 277 days.

This patent is subject to a terminal disclaimer.

(21) Appl. No.: 11/938,940

(22) Filed: Nov. 13, 2007

(65) Prior Publication Data

US 2008/0060988 A1 Mar. 13, 2008

Related U.S. Application Data

(62) Division of application No. 10/771,377, filed on Feb. 5, 2004, now Pat. No. 7,314,554.

(60) Provisional application No. 60/469,839, filed on May 13, 2003.

(30) Foreign Application Priority Data

Feb. 7, 2003 (IT) .......................... MI2003A0212

(51) Int. Cl.
*B01D 61/28* (2006.01)
*B01D 61/30* (2006.01)
*B01D 61/32* (2006.01)
*A61M 37/00* (2006.01)
*A61M 1/16* (2006.01)

(52) U.S. Cl. .................... 210/252; 210/258; 210/321.6; 210/416.1; 210/433.1; 604/4.01; 604/6.09; 604/6.11

(58) Field of Classification Search ................ 210/252, 210/253, 257.1, 257.2, 258, 321.6, 321.65, 210/321.71, 416.1, 433.1, 436, 472; 604/4.01, 604/5.01, 6.07, 6.09, 6.1, 6.11, 65, 66, 67
See application file for complete search history.

(56) References Cited

U.S. PATENT DOCUMENTS 3,909,045 A 9/1975 Meagher (Continued)

FOREIGN PATENT DOCUMENTS

AU 199870078 A1 1/1999

(Continued)

OTHER PUBLICATIONS

International Search Report for International Application No. PCT/IB2004/000062.

(Continued)

*Primary Examiner*—John Kim
(74) *Attorney, Agent, or Firm*—Finnegan, Henderson, Farabow, Garrett & Dunner, LLP

(57) ABSTRACT

The invention relates to an extracorporeal blood treatment machine in which a blood circuit (3) is equipped with an inlet line leading to a filtration unit (2) and with an outlet line (3b) from the filtration unit; a fluid circuit comprises an inlet line (4a) leading to the filtration unit and an outlet line (4b) from the filtration unit so as to allow a fluid taken from a primary container (5) to circulate within the filtration unit, thus enabling the treatment of the patient's blood. There is further an infusion line (6) acting on the outlet line of the blood circuit, which is supplied by an auxiliary fluid container (7). The inlet line of the fluid circuit is equipped with at least an infusion branch (8) acting on the outlet line of the blood circuit so as to enable the intensive therapy machine to manage therapies with large exchange of fluids.

19 Claims, 3 Drawing Sheets

U.S. PATENT DOCUMENTS

| | | | |
|---|---|---|---|
| 4,009,107 | A | 2/1977 | Miller et al. |
| 4,263,808 | A | 4/1981 | Bellotti et al. |
| 4,379,452 | A | 4/1983 | DeVries |
| 4,424,009 | A | 1/1984 | van Os |
| 4,436,620 | A | 3/1984 | Bellotti et al. |
| 4,526,515 | A | 7/1985 | DeVries |
| 4,637,813 | A | 1/1987 | DeVries |
| 4,844,810 | A | 7/1989 | Richalley et al. |
| 4,871,012 | A | 10/1989 | Kuo |
| 4,886,431 | A | 12/1989 | Soderquist et al. |
| 4,950,245 | A | 8/1990 | Brown et al. |
| 5,311,908 | A | 5/1994 | Barone et al. |
| 5,366,630 | A | 11/1994 | Chevallet |
| 5,427,509 | A | 6/1995 | Chapman et al. |
| 5,462,416 | A | 10/1995 | Dennehey et al. |
| 5,482,440 | A | 1/1996 | Dennehey et al. |
| 5,578,223 | A | 11/1996 | Bene et al. |
| 5,641,144 | A | 6/1997 | Hendrickson et al. |
| 5,679,245 | A | 10/1997 | Manica |
| 5,698,090 | A | 12/1997 | Bene et al. |
| 5,714,060 | A | 2/1998 | Kenley et al. |
| 5,722,399 | A | 3/1998 | Chevallet et al. |
| 5,910,252 | A | 6/1999 | Truitt et al. |
| 5,983,947 | A | 11/1999 | Utterberg |
| 6,277,277 | B1 | 8/2001 | Jacobi et al. |
| 6,308,721 | B1 | 10/2001 | Bock et al. |
| 6,325,775 | B1 | 12/2001 | Thom et al. |
| 6,730,233 | B2 | 5/2004 | Pedrazzi |
| 6,814,864 | B1 | 11/2004 | Favre et al. |
| 7,641,626 | B2 * | 1/2010 | Tonelli et al. .............. 604/4.01 |

FOREIGN PATENT DOCUMENTS

| | | |
|---|---|---|
| AU | 199870078 B2 | 1/1999 |
| EP | 0 134 436 B1 | 1/1988 |
| EP | 0 256 956 B1 | 2/1988 |
| EP | 0 116 596 B1 | 11/1990 |
| EP | 0 282 539 B1 | 1/1992 |
| EP | 0 611 227 A1 | 8/1994 |
| EP | 0 643 808 B1 | 1/1998 |
| EP | 0 695 397 B1 | 9/1998 |
| EP | 0 887 100 A1 | 12/1998 |
| EP | 0 893 603 A2 | 1/1999 |
| EP | 0 694 125 B1 | 2/1999 |
| EP | 0 686 237 B1 | 5/1999 |
| EP | 0 992 256 A2 | 4/2000 |
| EP | 0 679 099 B1 | 7/2001 |
| EP | 0 852 953 B1 | 11/2001 |
| GB | 2 076 476 A | 12/1981 |
| GB | 2 110 564 | 6/1983 |
| GB | 2 208 896 A | 4/1989 |
| JP | 5-192399 | 8/1993 |
| JP | 5-208048 | 8/1993 |
| JP | 6-315530 | 11/1994 |
| JP | 8-117332 | 5/1996 |
| WO | WO 80/02376 | 11/1980 |
| WO | WO 88/01895 | 3/1988 |
| WO | WO 95/17597 | 6/1995 |
| WO | WO 95/17598 | 6/1995 |
| WO | WO 95/17599 | 6/1995 |
| WO | WO 95/17600 | 6/1995 |
| WO | WO 95/17601 | 6/1995 |
| WO | WO 95/17602 | 6/1995 |
| WO | WO 95/17603 | 6/1995 |
| WO | WO 95/17604 | 6/1995 |
| WO | WO 97/02056 | 1/1997 |
| WO | WO97/10436 | 3/1997 |
| WO | WO 98/22163 | 5/1998 |
| WO | WO 99/13926 | 3/1999 |
| WO | WO 00/06292 | 2/2000 |
| WO | WO 01/08722 | 2/2001 |
| WO | WO 02/26288 A2 | 4/2002 |
| WO | WO 02/062454 | 8/2002 |

OTHER PUBLICATIONS

International Search Report for International Application No. PCT/IB2004/000104.

* cited by examiner

EXTRACORPOREAL BLOOD TREATMENT MACHINE

CROSS REFERENCE TO RELATED APPLICATIONS

This is a division of application Ser. No. 10/771,377, filed Feb. 5, 2004, now U.S. Pat. No. 7,314,554, issued on Jan. 1, 2008, and claims the priority of Italian Patent Application No. MI2003 A 000212, filed on Feb. 7, 2003, and the benefit of U.S. Provisional Application No. 60/469,839, filed May 13, 2003, the contents of which are incorporated herein by reference.

BACKGROUND OF THE INVENTION

The present invention relates to an extracorporeal blood treatment machine and to an integrated treatment module that can be used on said machine.

The object of the invention can be used for instance in intensive therapy machines which can carry out a plurality of different blood treatments.

Extracorporeal treatments generally consists in taking blood from the patient, in treating said blood when it is outside the patient's body and then in re-circulating the blood thus treated.

The treatment typically consists in removing from the blood unwanted and/or dangerous substances, as well as excess liquid in patients who cannot autonomously carry out said operations, such as for instances patients suffering from temporary or permanent kidney problems.

For instance, it may be necessary to add or remove substances from blood, to keep a correct acid/base ratio or also to remove fluid excess from the body.

The extracorporeal treatment is generally obtained by removing blood from the patient, by letting the blood flow within a filtration unit where a semipermeable membrane ensures the exchange of suitable substances, molecules and fluids.

Generally though not necessarily, said exchange is carried out by letting a given biological fluid ensuring the aforesaid exchanges pass in counter-current and within a secondary chamber of the filtration unit.

It should be noted that currently used machines can enable different types of blood treatment.

In the ultrafiltration treatment the substances and fluids to be eliminated are removed by convection from the blood, pass through the semipermeable membrane and are led towards the aforesaid secondary chamber.

In hemofiltration treatments part of the molecules, substances and fluids present in the blood pass through the membrane by convection as in the ultrafiltration treatment, although further necessary elements are added to the blood; typically a suitable fluid is infused directly into the blood before or after the latter passes through the filtration unit and anyhow before it is carried back into the patient.

In haemodialysis treatments a fluid containing material to be transferred into the blood is introduced into the secondary chamber of the filtration unit. The unwanted material flows through the semipermeable membrane from the blood into the secondary fluid and the desired substances/molecules from the secondary fluid can pass through the membrane as far as the blood.

In hemodiafiltration treatments the blood and the secondary fluid exchange their respective substances/molecules as in haemodialysis and, in addition, a fluid is infused into the blood as in haemofiltration treatments.

Obviously, in order to carry out each of said extracorporeal blood treatments, the blood has to be removed from a patient's vein or artery, suitably circulated in the machine and then re-introduced into the patient.

As is also known, blood treatment machines for intensive therapy have to be ready as fast as possible for an immediate use for any possible emergency.

Obviously, to this purpose the machine must not require either preliminary sanitizing operations or long pre-assembling operations of the various components for the various therapies.

As is known, intensive therapy machines are present on the market and are currently used, in which a blood circuit comprises a line for taking blood from the patient, which carries said blood to a filtration cartridge, and an outlet line from the filtration cartridge, which carries the treated blood back into the patient's body.

The machine is then equipped with a circuit for the passage of dialysis fluid; also said circuit has an intake line leading into the filtration unit, which is supplied by a sterile bag containing the dialysis liquid, and has also an outlet line enabling the passage of a fluid which has received by convection/diffusion the dangerous substances and molecules from the blood towards a collection bag for their subsequent removal.

Said machine is further equipped with an infusion line allowing—with suitable doses—to transfer directly into the blood upstream from the filtration unit the content of another liquid bag, thus adding the necessary products into the blood.

A known intensive therapy machine is further equipped with a suitable syringe containing for instance heparin as blood anticoagulant, the latter being added to the blood taken from the patient so as to avoid the creation of dangerous clots within the circuit.

The structure and circuitry mentioned above are generally defined by a single integrated module attached to the machine body.

It is evident that in order to enable the immediate use of the machine, the fluid bags referred to above have to be present and already sterile, so as to be directly and easily connected to their respective tubes, the latter also being sterile and disposable.

The machine is further equipped with a suitable control unit managing the flow of fluids by means of suitable peristaltic pumps and respective sensors associated to the circuit.

It is evident that by suitably setting the control unit said machine can selectively carry out one or more of the extracorporeal blood treatments described above (i.e. ultrafiltration, haemofiltration, haemodialysis and haemodiafiltration).

The machine described above, though being today quite a vanguard device for extracorporeal blood treatments in intensive therapies, has proved to be susceptible of several improvements.

In particular, a first intrinsic drawback in intensive therapy machines is related to the limited availability of fluids for operations involving the exchange of substances by convection/diffusion within the filter and for pre- or post-infusions into the blood line.

Said limitation is obviously related to the necessary use of pre-packaged sterile fluid bags typically containing 6 kg of dialysis liquid.

It is evident that the pre-established fluid amount to be used imposes some limitations, in particular in the case of therapies with large exchange of fluids, which would sometimes be extremely suitable in emergency cases.

On the other hand, it is not possible to use larger fluid amounts in intensive therapies since suitably treated water taken from the water network cannot be used as exchange fluid in short times; indeed, this would involve long operations for installing the devices for in-line preparation of sterile liquids; moreover, it is not possible to use bags with higher amounts of liquids due to the obvious problems involving transport and management of said containers by the personnel.

Another problem of known intensive therapy machines consists in achieving an optimal management of the administration of anticoagulant substances which are necessary for a good working of the machine.

In particular, today known intensive therapy machines cannot manage effectively the use of regional anticoagulation methods, such as for instance citrate-based methods, since the use of said techniques requires the administration of further solutions recovering the blood ion balance before carrying the treated blood back into the patient's body.

SUMMARY OF THE INVENTION

Under these circumstances the present invention aims at solving basically all the drawbacks referred to above.

A first technical aim of the invention is to provide physicians with the possibility to manage therapies with large exchange of fluids using an intensive therapy machine where, in any case, fluids are housed in small-size containers.

A further aim of the present invention is to be able to manage intensive therapies by using regional anticoagulation techniques, i.e. acting on the blood only in the extracorporeal circuit, without having to limit pre-infusion upstream from the filtration unit.

Moreover, an aim of the present invention is to enable the substantial separation of the use of regional anticoagulation techniques from the infusion of fluids for carrying out the necessary therapeutic exchange (by convection or diffusion).

Finally, an auxiliary aim of the present invention is to provide an machine ensuring quite simple and reliable loading and installing operations, further enabling the complete control of the therapy cycles that are carried out.

These and other aims, which shall be evident in the course of the present description, are basically achieved by an extracorporeal blood treatment machine as described in the appended claims.

Further characteristics and advantages will be clearer from the detailed description of a preferred though not exclusive embodiment of an extracorporeal blood treatment machine according to the present invention.

BRIEF DESCRIPTION OF THE DRAWINGS

This description will be given below with reference to the appended tables, which are provided as a mere guidance and are therefore not limiting, in which.

DETAILED DESCRIPTION

Figure 1:
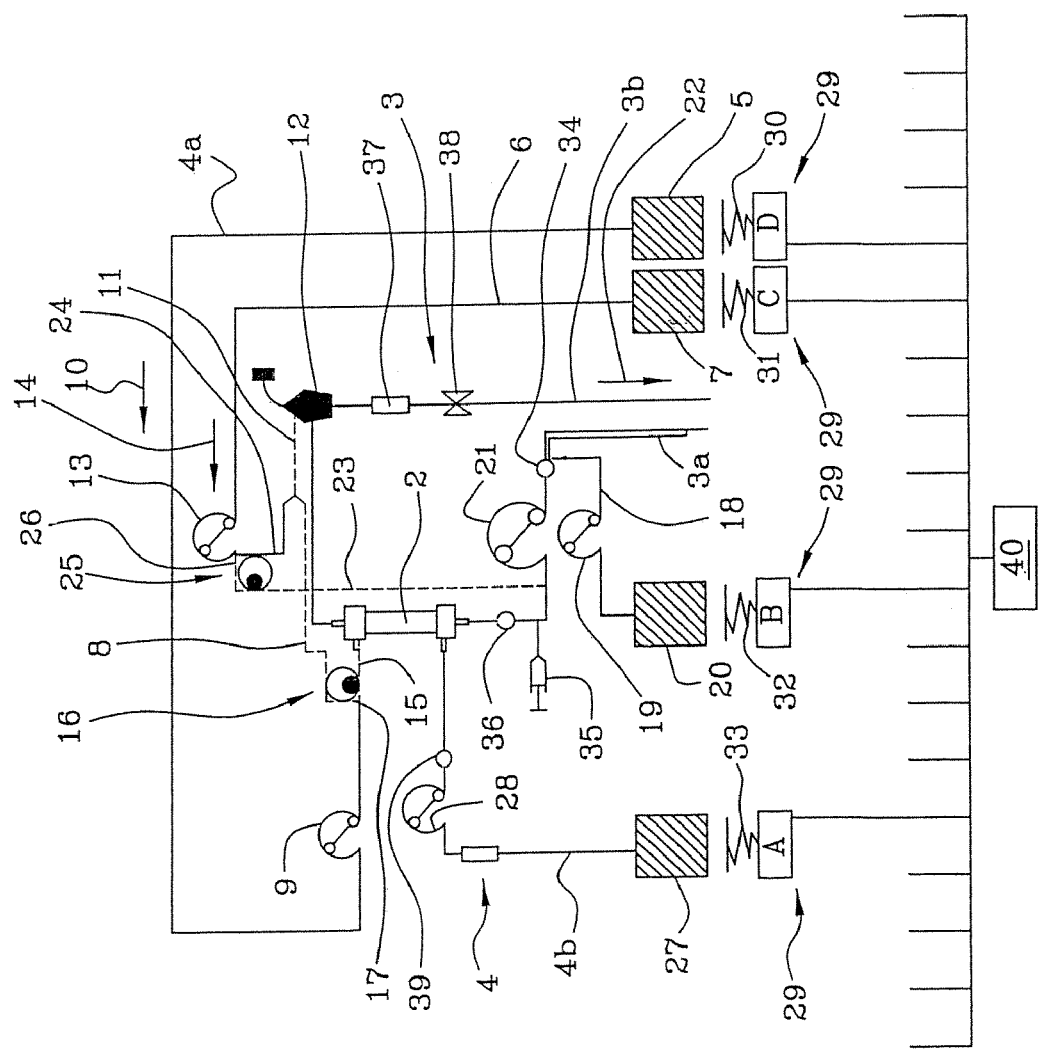
FIG. 1 shows schematically a hydraulic circuit to be used in an intensive therapy machine in accordance with the present invention.

With reference to the figures mentioned above, the numeral 1 globally refers to a machine for extracorporeal blood treatment, in particular for intensive therapies.

As can be inferred from the appended table 1, the machine consists of a blood circuit 3, which takes blood from a patient, for instance by means of a catheter introduced into a vein or artery of said patient, and through at least an inlet line 3a takes said blood, for instance continuously, to a filtration unit 2.

Then the blood passes through a primary chamber of said filtration unit 2 and through an outlet line 3b the treated blood is carried back to the patient.

The connection with an auxiliary pre-infusion line 18 is provided immediately downstream from the blood collecting zone on the inlet line 3a.

In particular, the machine is equipped with at least a secondary fluid container or bag 20 for supplying the pre-infusion line 18; by using corresponding means for conveying fluid, in the example shown comprising an auxiliary pre-infusion pump 19, for instance a peristaltic pump, it is possible to control the fluid flow within said line by introducing said fluid directly into the blood by means of a direct connection to the inlet line 3a.

Generally, the secondary fluid container 20 can house a suitable biological fluid for a pre-infusion, however said bag 20 can also contain an anticoagulant, generally causing a regional anticoagulation so as to ensure a particular working of the machine as shall be explained below in further detail.

After defining a direction of blood circulation 22 from the inlet line 3a towards the filtration unit and from the latter through the outlet line 3b towards the patient, a known blood pressure sensor 34, which shall not be described in further detail, is placed immediately downstream from the auxiliary pre-infusion line 18.

The blood circuit 3 therefore comprises means for conveying fluid, i.e. in this particular case at least a blood pump 21 for controlling and managing the suitable blood flow in the circuit. Also the blood pump 21 is generally a peristaltic pump.

Following the direction of blood circulation 22, there is then a device 35 for administering an anticoagulant, for instance a syringe containing suitable doses of heparin.

The blood then passes through another pressure sensor 36 controlling the correct flow within the blood circuit.

After passing through a main chamber of the filtration unit 2, where the suitable exchanges of substances, molecules and fluids occur by means of a semipermeable membrane, the treated blood enters the outlet line 3b first passing though a gas separating device (generally air) 12 commonly known as "bubble trap", designed so as to ensure the detection and removal of substances or air bubbles present in the blood.

The treated blood getting out of the separating device 12 then passes through an air bubble sensor 37 verifying the absence of said dangerous formations within the treated blood that has to be re-introduced in the patient's blood circulation.

Immediately downstream from the bubble sensor 37 there is an element 38 which, in case of alarm, can block the blood flow towards the patient.

In particular, should the bubble sensor 37 detect the presence of anomalies in the blood flow, the machine through the element 38 (be it a tap, a clamp or similar) would be able to block immediately the passage of blood so as to avoid any consequence to the patient.

Downstream from said element 38 the treated blood is then carried back to the patient undergoing therapy.

The extracorporeal blood treatment machine shown above is then equipped with a fluid circuit 4, which is also provided with at least an inlet line 4a leading into the filtration unit 2 and with an outlet line 4b from the filtration unit.

At least a primary fluid container 5 is designed to supply the inlet line 4a of the fluid circuit 4 (generally the primary fluid container 5 shall consist of a bag containing a suitable dialysis liquid).

The inlet line 4a then comprises means for conveying fluid such as at least a pump 9 (in the embodiment shown a peristaltic pump) for controlling the flow of liquid from the bag 5 and for defining a direction of circulation 10.

Downstream from the pump 9 in the direction of circulation 10 there is a branching 17 splitting the fluid circuit 4 up into an intake branch 15 and an infusion branch 8.

In particular, the infusion branch 8 is connected to the outlet line 3b of the blood circuit 3.

In other words, by means of said infusion branch 8 it is possible to obtain a post-infusion directly in the blood line using the content of the primary fluid container 5.

Conversely, the intake branch 15 conveys the fluid directly to the filtration unit and in particular to a secondary chamber of said unit.

The fluid circuit 4 is further equipped with selecting means 16 for determining the percentages of fluid flow within the infusion branch 8 and the intake branch 15.

Generally said selecting means 16, usually placed near the branching 17, can be positioned at least between a first operating condition in which they allow the passage of fluid in the intake branch 15 and block the passage in the infusion branch 8, and a second operating condition in which they allow the passage of fluid in the infusion branch 8 and block the passage in the intake branch 15.

In other words, said selecting means 16 can consist of a valve element operating on the fluid circuit 4 by alternatively blocking the passage of fluid in either branch.

It is also evident that it might be provided for suitable selectors, which are able to establish a priori the amount of liquid that has to pass through both branches simultaneously.

It will also be possible to vary the percentages of fluid in either branch as a function of time and of the pre-established therapies.

The dialysis liquid through the intake branch 15 gets into a secondary chamber of the filtration unit 2.

In particular, the primary chamber through which the blood flow passes is separated from the secondary chamber through which the dialysis liquid passes by means of a semipermeable membrane ensuring the suitable passage of the dangerous substances/molecules and of fluid from the blood towards the dialysis liquid mainly by means of convection and diffusion processes, and also ensuring through the same principles the passage of substances/molecules from the dialysis liquid towards the blood.

The dialysis fluid then gets into the outlet line 4b and passes through a suitable pressure sensor 39 whose function is to control the working of said line.

Then there are means for conveying fluid, for instance a suction pump 28 controlling the flow in the outlet line 4b within the fluid circuit 4. Also said pump will generally be a peristaltic pump.

The fluid to be eliminated then passes through a blood detector and is conveyed into a collection container or bag 27.

Further analyzing the particular circuit of the machine according to the invention, note the presence of at least another infusion line 6 acting on the outlet line 3b of the blood circuit 3.

In particular, the infusion fluid is taken from at least an auxiliary container 7 and is sent directly to the outlet line 3b of the blood circuit 3 through means for conveying fluid, generally an infusion pump 13 controlling its flow (in the example a peristaltic pump).

In particular and as can be observed in the appended figure, the infusion liquid can be introduced directly into the gas separating device 12.

As can also be inferred, the infusion branch 8 of the fluid circuit 4 and the infusion line 6 are equipped with a common end length 11 letting into the blood circuit 3.

Said intake end length 11 is placed downstream from the infusion pump 13 with respect to a direction of infusion 14 and carries the fluid directly into the bubble trap device 12.

Further referring to the diagram in FIG. 1, one can notice the presence within the infusion line 6 of at least a pre-infusion branch 23 connected to an inlet line 3a of the blood circuit 3.

In further detail, downstream from the infusion pump 13 with respect to the direction of infusion 14, there is a branching 26 splitting the infusion line 6 up into pre-infusion branch 23 and post-infusion branch 24.

The pre-infusion branch 23, in particular, carries the fluid taken from the bag 7 on the inlet line 3a of the blood circuit down-stream from the blood pump 21 with respect to the direction of circulation 22.

Conversely, the post-infusion branch 24 is connected directly to the common end length 11.

The infusion line 6 further comprises selecting means 25 for determining the percentage of liquid flow to be sent to the post-infusion branch 24 and to the pre-infusion branch 23.

The selecting means 25 placed near the branching 26 can be positioned between at least a first operating condition in which they allow the passage of fluid in the pre-infusion branch 23 and block the passage in the post-infusion branch 24, and at least a second operating condition in which they allow the passage of fluid in the post-infusion branch 24 and block the passage in the pre-infusion branch 23.

Obviously, as in the case of the selecting means 16 present on the fluid circuit 4, also the other selecting means 25 will be able to determine the percentage of fluid that has to pass in each of the two branches and to possibly vary it in time in accordance with the planned therapies. Moreover, the selecting means 16 and the other selecting means 25 will generally though not necessarily be of the same nature.

The machine is then equipped with means 29 for determining at least the weight of the primary fluid container 5 and/or of the auxiliary fluid container 7 and/or of the secondary fluid container 20 and/or of the collection container 27.

In particular, said means 29 comprise weight sensors, for instance respective scales 30, 31, 32 and 33 (at least an independent one for each fluid bag associated to the machine).

In particular, there will be at least 4 of said scales, each pair being independent from the other, and each one measuring the respective weight of a bag.

It should then be pointed out that there is a processing unit or CPU 40 acting on the blood circuit 3 and in particular on the pressure sensor 34, on the blood pump 21, on the device 35 for heparin infusion, on the other pressure sensor 36, and on the device for detecting the presence of air bubbles 37 and on its respective closing element 38.

Said CPU 40 has also to control the fluid circuit 4 and, in particular, shall be input with the data detected by the scales 30 and concerning the weight of the bag 5 and shall act on the pump 9, on the selecting means 16, on the pressure sensor 39, then on the suction pump 28 and shall eventually receive the data detected by the scales 33 whose function is to determine the weight of the collection container 27.

The CPU 40 shall also act on the infusion line 6 checking the weight of the auxiliary container 7 (checked by the scales 31) and will be able to control both the infusion pump 13 and the other selecting means 26.

Eventually, the CPU 40 shall also act on the auxiliary pre-infusion line 18 detecting the weight of the secondary fluid container 20 by means of the scales 32 and suitably controlling the pump 19 according to the treatments to be carried out.

Reminding that the above description has been made with the sole purpose of describing the whole of the hydraulic circuit of the extracorporeal blood treatment machine, here is a short description of the working of the device.

Once the whole hydraulic circuit and the filtering unit 2 have been correctly associated to the machine so that the various peristaltic pumps engage the respective lengths of tubes and that all the sensors have been suitably positioned, and the various bags containing the various fluids have been associated to the corresponding liquid supply/intake lines, and the blood circuit has been connected to a patient's artery/vein, the initial circulation of blood within its circuit is enabled.

Therefore, according to the kind of therapy that has been set, the extracorporeal blood treatment machine is automatically started and controlled by the processing unit 40.

If the patient undergoes an ultrafiltration treatment, as well as the blood pump 21 the suction pump 28 connected to the outlet line of the fluid circuit 4 is started, so as to take by convection a fluid excess in the patient by means of the filtration unit.

Conversely, if the therapy that has been set comprises a haemofiltration treatment, as well as the blood pump 21 and the suction pump 28 for taking fluids by convection also the pump 9 on the inlet line of the fluid circuit 4 and the selecting means 16 placed so as to enable a post-infusion are started.

Also the infusion line 6 shall be used so as to enable a further addition of liquids to the post-infusion or to enable a suitable pre-infusion.

Conversely, if the treatment involves haemodialysis, the pumps 9 and 28 of the fluid circuit 4 shall be started and the selecting means 16 shall be positioned so as to ensure the passage of the dialysis liquid only towards the filtration unit 2 so as to take substances and/or molecules and/or liquids by diffusion and possibly by convection if the transmembrane pressure through the filtration unit is other than zero.

Eventually, if a haemodiafiltration treatment has to be carried out, beyond the blood pump 21 the fluid circuit and therefore the pumps 9 and 28 shall be started, so as to ensure a circulation of the liquid within the filtration unit 2 and also the pump 14 of the infusion line 6 shall be started so as to ensure a pre- or post-infusion.

It will be possible to set up therapies comprising one or more of the treatments referred to above.

In all the treatments described above, possibly except the ultrafiltration treatment, it will be possible to use the auxiliary pre-infusion line for introducing an anticoagulant and/or a suitable infusion liquid into the blood.

The anticoagulant can also be administered by means of the suitable device 35 designed for the introduction of heparin into blood.

Concerning this it should be pointed out that the machine according to the invention is designed to receive various kinds of syringes according to the amount of anticoagulant to be administered.

Obviously, it is the control unit 40 that, being connected to the various devices, sensors, pumps and being input with the data on weight from the scales, is able—once it is set—to control and automate the whole working of the machine.

In further detail, it is possible to set the flows of the various pumps present on the machine in accordance with the therapy or therapies to be started.

Obviously, the setting of said flows results in an amount of fluid taken from the patient (weight loss), which will generally be given by the difference between the weight of the liquid that has been collected in the bag 27 and of the liquid circulated in the circuit through the primary fluid container 5, the auxiliary fluid container 7 and the secondary fluid container 20.

In particular, in accordance with the data received by the control unit coming from the various scales (and the theoretical flow rates fixed on each pump of therapy/treatment carried out) the control unit 40 shall control the means for circulating fluid in the various lines by suitably varying the thrust exerted by the various pumps 9, 13, 19, 21 and 28.

In particular, the signals coming from the scales referred to above 30, 31, 32, 33 are used by the control unit 40 for determining the weight of the particular fluid introduced into the line or collected.

In order to determine the amount of fluid released or collected in a particular bag or container the control unit 40 compares at regular intervals (the greater the flows the smaller the intervals) the actual weight of the container with the desired weight (which is a direct function of the desired flow for each pump and of the time interval between each control step $\Delta W = Q \Delta t$).

The desired weight can be calculated as a function of the required flow (stored in a suitable storage unit of the computer) and of the time elapsed from the beginning of the treatment.

If the actual weight and the desired weight differ from each other, the control unit acts on the corresponding pump so as to reduce, and possibly cancel, said difference. In other words, during each cycle not an absolute weight variation, but only the variation in the time interval is taken into consideration to correct the latter.

The control unit takes into consideration variations in the difference starting from the last comparison, so as to avoid oscillations of the actual flow around the desired flow.

Figure 3:
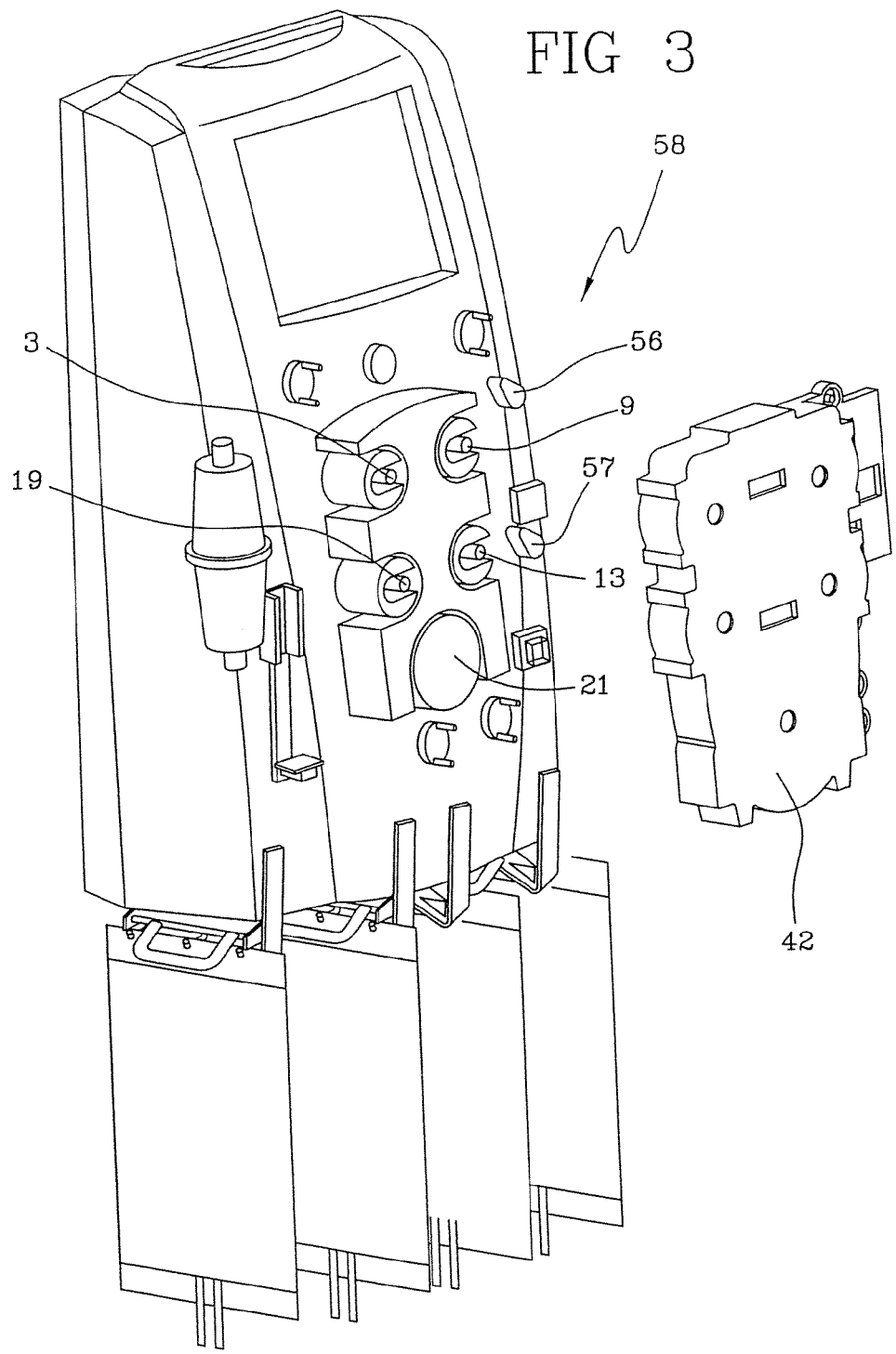
FIG. 3 shows an machine body in accordance with the invention.

Reminding that the above description has been carried out with the sole purpose of providing a general view of the blood treatment machine and of the hydraulic circuit thereto associated, it should be noted that generally the whole machine shall comprise a body 58 (see in particular FIG. 3) designed to integrate all instruments and devices to be used several times in different treatments on one or more patients.

In particular, the machine body 58, beyond the whole electronic control circuitry (processing unit 40, data input and reading display, pressure sensors 34, 36, 39, . . . ) shall also have on its front surface the blood pump 21, the fluid pump 9, the infusion pump 13 and the auxiliary pre-infusion pump 19.

Conversely, the parts of the machine that are designed to be used only once for each treatment on the patient, generally in the course of an intensive therapy, shall be housed in a corresponding disposable integrated module 41 to be attached directly onto the machine body 58.

Figure 2:
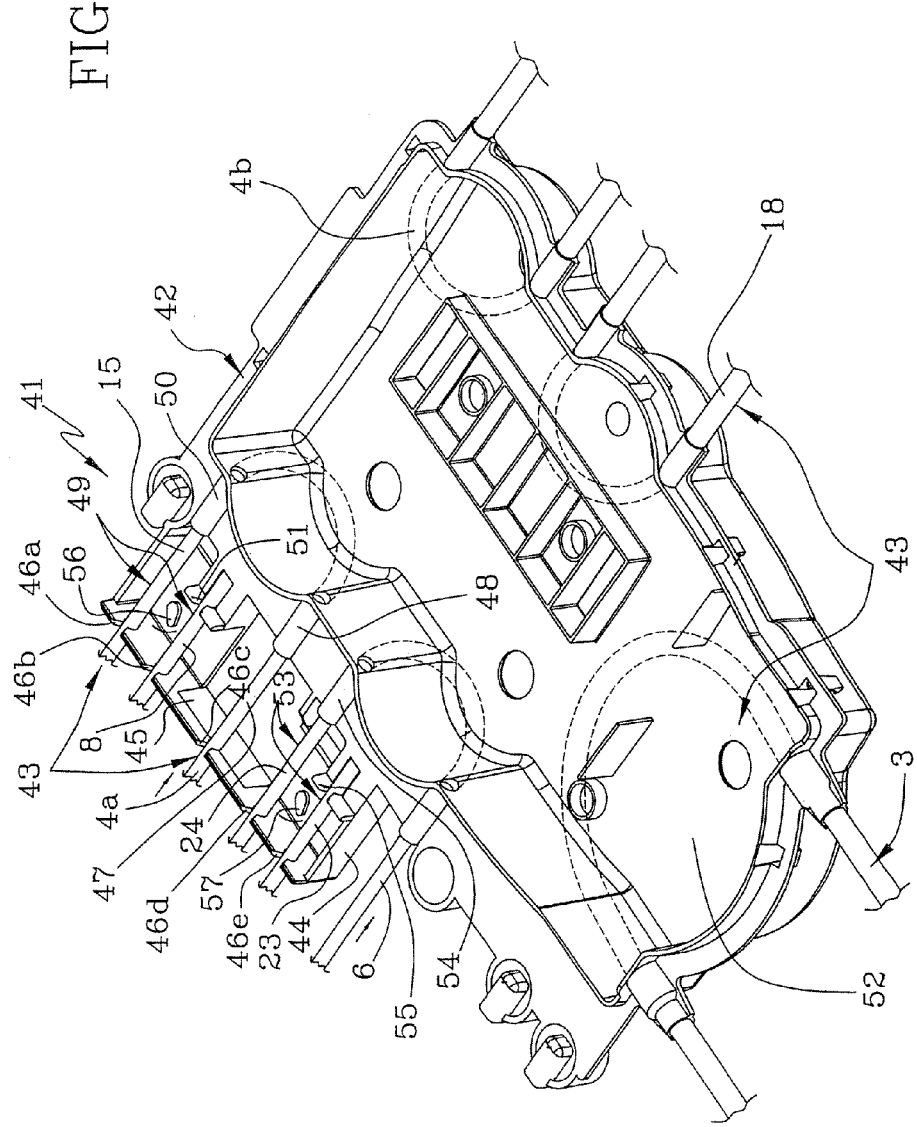
FIG. 2 shows an integrated module comprising a support element and a portion of the fluid distribution circuitry, to be used in intensive therapy machines in accordance with the pre-sent invention.

As shown in FIG. 2, the integrated module 41 for blood treatment has a support element 42 consisting of a main body 52 and of a supporting structure 44 associated, for instance as one piece, to the main body and placed laterally with respect to the latter.

Said integrated module further comprises a fluid distribution circuitry 43 (represented only partially in the appended FIG. 2) associated to said support element 42 and cooperating with the filtration unit 2 so as to carry out the hydraulic circuit previously described.

In particular, it is possible to note how the main body 52 defines a housing compartment designed to receive the respective U-arranged lengths of tubes of the circuitry, which are kept in position so as to be ready to cooperate with the respective peristaltic pumps housed by the machine body 58.

As can be observed, the blood circuit 3 and in general the inlet line 3a of the blood circuit 3 is fastened by means of connectors to a side wall of the main body 52, in the same way as also the inlet line 4a of the fluid circuit 4 and the outlet line 4b of the fluid circuit 4 are secured to the main body 52.

Also the infusion line 6 and the auxiliary pre-infusion line 18 are secured to the main body 52 (see again FIG. 2).

All the portions of lines referred to above are secured to the support element 42 so as to define at least a corresponding U-arranged length of tube with respect to said support element 42 and so that each of said U-lengths can cooperate with the corresponding peristaltic pump housed in the machine body.

Going into further constructive details, it can be noted how the support structure 44 comprises a positioning fin 45 provided with a given number of main seats 46a, 46b, 46c, 46d and 46e suitably placed so that respective tubes of the fluid distribution circuit 43 associated to the support element can be engaged therein.

As can be further observed, the inlet line 4a of the fluid circuit 4 is fastened to the main body 52 on the support structure 44.

As a matter of fact, at least an inlet length 47 is kept in position by the support structure 44 by means of a main seat 46c of the positioning fin 45 and by a corresponding connector 48 defined on the main body.

The outlet length 49 of the fluid circuit 4 is engaged in its turn with the respective engagement connector 50 and with the main seat 46a of the positioning fin 45.

As can be noted from the arrangement shown, the inlet and outlet lengths 47 and 49 engaged to their respective connectors 48, 50 and with the main seats 46c and 46a are placed in a substantially rectilinear arrangement and are parallel one to the other.

It should then be pointed out that the outlet length 49 has a branching 17 splitting up into intake branch 15 designed to convey the fluid to the filtration unit, and infusion branch 8 designed to convey the fluid to the blood circuit 3.

Said branching 17 cannot be seen in FIG. 2 since it is defined by the engagement connector 50 on the opposite side with respect to the one shown in said figure.

In other words, the connector 50 has a basically T shape, whose two outlets are connected to the intake branch 15 and to the infusion branch 8.

The infusion branch 8 is further secured to an auxiliary seat 51 of the support structure and to another main seat 46b.

When engaged the infusion branch 8 and the intake branch 15 are placed in a rectilinear arrangement and are parallel one to the other.

Also the infusion line 6 is fastened to the main body 52 on the support structure 44.

At least an outlet length 53 of the infusion line 6 is engaged to a main seat 46d of the positioning fin and to a respective engagement connector 54.

Analogously to the above description, also the outlet length 53 of the infusion line 6 has a branching 26 splitting up into pre-infusion branch 23 designed to convey the fluid to the inlet line 3a of the blood circuit 3, and post-infusion branch designed to convey the fluid to the outlet line 3b of the blood circuit 3.

Here again the branching 26 is not shown in FIG. 2 since it is defined by the T-shaped connector 54, one of whose outlets can be seen only on the opposite side with respect to the one shown.

The pre-infusion branch 23 is secured to an auxiliary seat 55 of the support structure and to another main seat 46e of the fin 45.

Said arrangement enables to have pre-infusion branch 23 and post-infusion branch 24 in rectilinear configuration and parallel one to the other.

It should now be observed that the selecting means 16 previously defined act by enabling or blocking the passage of fluid in the infusion branch 8 and/or in the intake branch 15 exactly on the rectilinear lengths defined on the support structure 44.

In particular, said selecting means 16 can be defined by suitable cams or clamps.

The example of embodiment shown provides for a moving element 56, which as a result of its movement blocks either the infusion branch 8 or the intake branch 15.

Said moving element 56 is generally mounted directly onto the machine body 58 and has been shown with a mere explicative purpose and with a hatched line in the appended FIG. 2.

Wholly similarly, the other selecting means 25 can comprise a moving element 57 acting on the pre-infusion branch 23 or on the post-infusion branch 24 for selectively blocking or enabling the passage of fluid.

Here again said moving element 57 has been shown by way of example in FIG. 2; however, it should be noted that generally said element is mounted directly onto the machine body 58.

The invention has important advantages.

It is obvious that the use of a hydraulic circuit enabling a passage of the dialysis fluid within the filtration unit or selectively towards a post-infusion by using the same liquid coming from the primary fluid bag 5, allows to manage therapies with a large volume of fluids, particularly in intensive therapy machines where anyhow said fluids are housed in small bags.

As a matter of fact, it will be possible to carry out a pre- and/or post-infusion into the blood line using the fluid of the primary container 5 and of the auxiliary container 7, thus carrying out for instance a more intense ultrafiltration.

Moreover, the presence of a branching also on the infusion line allows to manage therapies with regional anticoagulation techniques without limiting the possibilities of dialysis pre-filter infusion in any way.

When regional anticoagulation techniques are used, such as for instances the use of citrates, it is always necessary, before carrying the treated blood back into the patient, to administer to the latter suitable substances (for instance calcium) for recovering the ion balance in the blood.

It is obvious that the elimination/balance of the anticoagulant substances should be carried out downstream from the filtration unit, for instance by means of the post-infusion line.

In the machine according to the invention, however, in order to balance the ions in the returned blood it will be possible to use directly the fluid circuit by introducing a suitable reagent into the primary fluid bag 5 and by using the inlet line 4a for carrying out the post-infusion through the infusion branch 8.

The infusion line 6 shall thus enable to carry out pre-infusions, ensuring the optimal working of the machine also during this kind of treatments.

Therefore, the particular arrangement of the pre- and post-infusion lines and of the dialysis lines enables—also in intensive therapy machines where all the various fluids are contained in small bags—to carry out all the necessary therapies/treatments, thus eliminating the operational limits present in known machines.

The invention claimed is:

1. An integrated module for blood treatment, comprising:
   a support element;
   at least one filtration unit engaged to the support element; and
   a fluid distribution circuitry associated to the support element and cooperating with the filtration unit, said fluid distribution circuitry including:
   a plurality of tubes;
   a blood circuit having at least an inlet line connected to the filtration unit, and an outlet line connected to said filtration unit;
   a fluid circuit having at least an inlet line connected to the filtration unit, and an outlet line connected to the filtration unit, the inlet line of the fluid circuit being designed to be connected to at least a primary fluid container; and
   at least an infusion line acting on the outlet line of the blood circuit, said infusion line being designed to be supplied by at least an auxiliary fluid container, and the infusion line being fastened to the support element so as to define at least a U-arranged tube length with respect to said support element, at least an outlet length of the infusion line having a branching splitting up into pre-infusion branch conveying fluid to the inlet line of the blood circuit, and into post-infusion branch conveying fluid to the outlet line of the blood circuit;
   wherein the inlet line of the fluid circuit comprises at least an infusion branch connected to the outlet line of the blood circuit, the inlet line of the fluid circuit being fastened to the support element so as to define at least a U-arranged tube length with respect to said support element, at least an outlet length of the inlet line of the fluid circuit having a branching splitting up into intake branch conveying the fluid to the filtration unit, and into the infusion branch, separate from the post-infusion branch of the infusion line, conveying the fluid to a blood circuit.

2. A module according to claim 1, wherein the support element comprises a main body and a support structure associated to the main body and placed laterally with respect to the latter.

3. A module according to claim 2, wherein the support structure comprises a positioning fin having a given number of main seats in which each of the tubes of the fluid distribution circuit are respectively engaged.

4. A module according to claim 1, wherein the inlet line of the fluid circuit is fastened to the support element so as to define at least a U-arranged tube length with respect to said support element, which shall cooperate operationally with a respective pump.

5. A module according to claim 3, wherein the inlet line of the fluid circuit is fastened to the main body on the support structure so as to define at least a U-arranged tube length with respect to said support structure, which shall cooperate operationally with a respective pump, at least an inlet length of the inlet line of the fluid circuit being engaged in a main seat of the positioning fin and to a respective engagement connector on the main body, at least an outlet length of the inlet line of the fluid circuit being engaged in a main seat of the positioning fin and to the respective engagement connector.

6. A module according to claim 5, wherein the inlet and outlet lengths engaged to the connectors and to the main seats are placed in a rectilinear arrangement and are parallel one to the other.

7. A module according to claim 5, wherein the outlet length has a branching splitting up into intake branch conveying the fluid to the filtration unit, and into infusion branch conveying the fluid to a blood circuit.

8. A module according to claim 7, wherein the branching splitting up into infusion branch and intake branch is defined on an engagement connector.

9. A module according to claim 7, wherein the infusion branch is secured to an auxiliary seat and to another main seat.

10. A module according to claim 7, wherein the infusion branch and the intake branch are placed in a rectilinear arrangement and are parallel one to the other.

11. A module according to claim 1, wherein the infusion line is secured to the support element so as to define at least a U-arranged tube length with respect to said support element, said tube length being designed to cooperate operationally with a respective pump.

12. A module according to claim 3, wherein the infusion line is fastened to the main body on the support structure so as to define at least a U-arranged tube length with respect to said support element, at least an outlet length of the infusion line being engaged to a main seat of the positioning fin and to a respective engagement connector on the main body.

13. A module according to claim 12, wherein the outlet length has a branching splitting up into pre-infusion branch conveying fluid to the inlet line of the blood circuit, and into post-infusion branch conveying fluid to the outlet line of the blood circuit.

14. A module according to claim 13, wherein the branching splitting up into pre-infusion branch and post-infusion branch is defined on an engagement connector.

15. A module according to claim 13, wherein the pre-infusion branch is secured to an auxiliary seat and to another main seat.

16. A module according to claim 14, wherein the pre-infusion branch and the post-infusion branch are placed in a rectilinear arrangement and are parallel one to the other.

17. A module according to claim 1, further comprising an auxiliary pre-infusion line acting on the inlet line of the blood circuit and having at least a pre-infusion branch connected to the inlet line of the blood circuit.

18. An integrated module for blood treatment, comprising:
    a support element presenting a main body and a support structure associated to the main body and placed laterally with respect to the latter, the support structure comprising a positioning fin having a given number of main seats;
    at least one filtration unit engaged to the support element; and
    a fluid distribution circuitry associated to the support element and cooperating with the filtration unit, said fluid distribution circuitry including:
    a blood circuit having at least an inlet line connected to the filtration unit, and an outlet line connected to said filtration unit;
    a fluid circuit having at least an inlet line connected to the filtration unit, and an outlet line connected to the filtration unit, the inlet line of the fluid circuit being designed to be connected to at least a primary fluid container, the inlet line of the fluid circuit comprises at least an infusion branch connected to the outlet line of the blood circuit, an inlet length of the inlet line is engaged on a main seat of the positioning fin and to a connector of the main body, an outlet length of the inlet line is engaged with a connector on the main body and with a main seat on the positioning fin, the infusion branch being in engagement with a main seat of the positioning fin; and at least an infusion line fastened to the main body and acting on the outlet line of the blood circuit, said infusion line being designed to be supplied by at least an auxiliary fluid container, at least an outlet length of the infusion line having a branching splitting up into pre-infusion branch conveying fluid to the inlet line of the blood circuit, and into post-infusion branch conveying fluid to the outlet line of the blood circuit, the outlet length of the infusion line being engaged to a main seat of the positioning fin and to an engagement connector of the main body, the pre-infusion branch is secured to another main seat of the positioning fin.

19. The module according to claim 18, wherein the inlet and outlet lengths engaged to the connectors and to the main seats are placed in a rectilinear arrangement and are parallel one to the other.

* * * * *